US005624788A

United States Patent [19]
Murai et al.

[11] Patent Number: 5,624,788
[45] Date of Patent: Apr. 29, 1997

[54] ORGANIC SILICON COMPOUND, RESIST THERMAL POLYMERIZATION COMPOSITION AND PHOTOPOLYMERIZATION COMPOSITION

[75] Inventors: Shinji Murai, Ichikawa; Yoshihiko Nakano; Ken Uchida, both of Tokyo; Shuji Hayase, Yokohama, all of Japan

[73] Assignee: Kabushiki Kaisha Toshiba, Kawasaki, Japan

[21] Appl. No.: 490,614

[22] Filed: Jun. 15, 1995

[30] Foreign Application Priority Data

Jun. 16, 1994 [JP] Japan .................... 6-134095

[51] Int. Cl.$^6$ ............... G03F 7/004; G03F 7/023; G03F 7/027; G08G 77/00
[52] U.S. Cl. ............ 430/270.1; 430/170; 430/192; 430/281.1; 430/288.1; 522/31; 522/148; 528/40; 528/43
[58] Field of Search ............... 430/270.1, 281.1, 430/288.1, 192, 170; 528/40, 43; 522/31, 148

[56] References Cited

U.S. PATENT DOCUMENTS

| | | | |
|---|---|---|---|
| 5,017,453 | 5/1991 | Onishi et al. | 430/270.1 |
| 5,130,392 | 7/1992 | Schwalm et al. | 430/270.1 |
| 5,350,660 | 9/1994 | Urano et al. | 430/270.1 |
| 5,352,564 | 10/1994 | Takeda et al. | 430/270.1 |
| 5,372,908 | 12/1994 | Hayase et al. | 430/270 |

FOREIGN PATENT DOCUMENTS 1-311102  12/1989  Japan .

OTHER PUBLICATIONS

R.D. Miller, et al.; Polysilanes: Photochemistry and Deep UV Lithography, 1989 vol. 29, No. 13, pp. 882–886.
Robert D. Miller, et al., Polysilane High Polymers, 1989, vol. 89, No. 6, pp. 1359–1410.

*Primary Examiner*—John S. Chu
*Attorney, Agent, or Firm*—Oblon, Spivak, McClelland, Maier & Neustadt, P.C.

[57] ABSTRACT

Disclosed are an organic silicon compound having a repeating unit represented by general formula (I) shown below, a resist, a thermal polymerization composition and a photopolymerization composition containing the organic silicon compound.

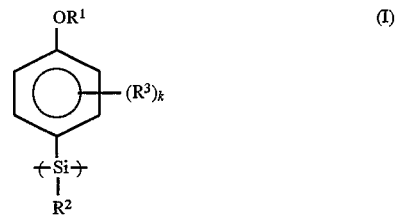

wherein $R^1$ is a t-butyl group or a tetrahydropyranyl group, $R^2$ is an hydrogen atom, a substituted or unsubstituted alkyl group having 1 to 24 carbon atoms, a substituted or unsubstituted aryl group having 1 to 24 carbon atoms, or a substituted or unsubstituted aralkyl having 7 to 24 carbon atoms, $R^3$ is a substituted or unsubstituted alkyl group having 1 to 24 carbon atoms, a substituted or unsubstituted aryl group having 6 to 24 carbon atoms, a substituted or unsubstituted aralkyl group having 7 to 24 carbon atoms or an alkoxyl group, and k represents an integer from 0 to 4.

13 Claims, 4 Drawing Sheets

ORGANIC SILICON COMPOUND, RESIST THERMAL POLYMERIZATION COMPOSITION AND PHOTOPOLYMERIZATION COMPOSITION

BACKGROUND OF THE INVENTION

1. Field of the Invention

The present invention relates to an organic silicon compound which can be easily decomposed by light, heat or acid. The invention is also related to a resist, a thermal polymerization composition and a photopolymerization composition using the organic silicon compound.

2. Description of the Related Art

Polysilane is an organic silicon compound having an Si—Si structure as a main chain and usually a hydrophobic group such as an alkyl group or an aryl group as a side chain, which is photoreactive since σ electrons of the Si—Si bond are delocalized. For its photoreactivity, the polysilane is expected to be used as a resist and a photopolymerization initiator for a long time.

For example, Jpn. Pat. Appln. KOKOKU Publication No. 3-79377, discloses a polysilane which may be employed as a positive-working resist. However, the conventional polysilane is not sufficiently photoreactive, it can hardly serve to form high-precision fine patterns when it is used singly as photoresist.

Journal of Radiation Curing, January 1986, pp. 35–40, discloses an attempt to use a polysilane as a polymerization catalyst for a compound having an unsaturated bond, taking advantage of the fact that the polysilane having an alkyl group or aryl group as a side chain is decomposed upon exposure to light and generates radical species. Unfortunately, this attempt accompanies the problem that the polymerization efficiency is not always at a satisfactory level.

SUMMARY OF THE INVENTION

Hitherto, the application of polysilane to a resist and a polymerization catalyst have been aggressively studied, taking advantages of the above-mentioned characteristics of the polysilane in that the Si—Si bond of the polysilane can be decomposed upon exposure to light. However, none of the conventional polysilanes are not practically used due to the difficulty in decomposing the Si—Si bond.

An object of the present invention is to provide an organic silicon compound represented by a polysilane, which is easily decomposed by light, heat or acid, and particularly suitable for resist, and a polymerization catalyst for a compound having an unsaturated bond.

Another object of the present invention is to provide a resist capable of forming a high-precision and high-resolution pattern, and further to provide a thermal polymerization composition and a photopolymerization composition having sufficient polymerization efficiency, using the organic silicon compound mentioned above.

The organic silicon compound of the present invention has a repeating unit represented by general formula (I) shown below:

wherein $R^1$ is a t-butyl group or a tetrahydropyranyl group, $R^2$ is an hydrogen atom, a substituted or unsubstituted alkyl group having 1 to 24 carbon atoms, a substituted or unsubstituted aryl group having 6 to 24 carbon atoms, or a substituted or unsubstituted aralkyl group having 7 to 24 carbon atoms, $R^3$ is a substituted or unsubstituted alkyl group having 1 to 24 carbon atoms, a substituted or unsubstituted aryl group having 6 to 24 carbon atoms, a substituted or unsubstituted aralkyl group having 7 to 24 carbon atoms or an alkoxyl group, and k represents an integer from 0 to 4.

The resist of the present invention comprises an organic silicon compound having a repeating unit represented by the aforementioned general formula (I). The resist of the present invention may contain a compound which generates an acid upon exposure to light together with the aforementioned organic silicon compound.

The thermal polymerization composition or photopolymerization composition of the present invention contains a compound having an unsaturated bond and the aforementioned organic silicon compound.

DETAILED DESCRIPTION OF THE PREFERRED EMBODIMENT

The organic silicon compound of the present invention has a specific structure such that a t-butyl group or a tetrahydropyranyl group is introduced, via an ether bond, to the p-position of a benzene nucleus of a side chain directly binding to Si. Hereinbelow such an organic silicon compound of the present invention will be described in detail.

The organic silicon compound of the present invention may be either a monomer or polymer. Although the organic silicon compound of the present invention is not limited by a molecular weight thereof, a degree of polymerization thereof is preferably set appropriately so as to meet the uses.

To be more specific, when the organic silicon compound of the present invention is used for resist, the degree of polymerization is preferably from 5 to 50,000, and more preferably from 20 to 10,000. This range is defined for the following reasons: If the degree of polymerization of the organic silicon compound is extremely low, it will be difficult to form resist having sufficient durability. In contrast, if the degree of polymerization is extremely high, the solubility of the organic silicon compound in an organic solvent will reduce.

When the organic silicon compound of the present invention is used as a radical polymerization catalyst (radical initiator) for a compound having an unsaturated bond, the degree of polymerization is preferably from 1 to 50,000, and more preferably, from 5 to 10,000. This range is defined for the following reasons: If the degree of polymerization of the organic silicon compound is extremely high, the compatibility of the organic silicon compound and the compound having an unsaturated bond will reduce, resulting in non-uniform polymerization. In the organic silicon compound of the present invention, an Si—Si bond thereof can be readily decomposed by light or heat and generates radicals with high efficiency. At this time, radicals are additionally generated by cleavage of a bond between Si and a benzene nucleus of a side chain. Therefore, even a monomer having alkyl groups having 1 to 16 carbon atoms at both ends of the Si atom shown in general formula (I) can be used as a polymerization catalyst for the compound having an unsaturated bond since it generates radicals. However, since the efficiency of radical generation is low in a monomer or an oligomer with a low degree of polymerization, it is desired to use an organic silicon compound having a degree of polymerization of 5 or more as mentioned above.

The organic silicon compound of the present invention can be synthesized by, for example, the following method:

First, an organic silicon compound having a repeating unit represented by general formula (1) is prepared as a raw material. In the case where a polymer of the organic silicon compound, i.e., polysilane, is used, the polysilane may be polymerized in accordance with a method of reacting a monomer of dihalosilane corresponding to general formula (1) with a metal sodium in an appropriate solvent. After the starting organic silicon compound is dissolved in an organic solvent such as chloroform, trifluoromethanesulfonic acid is added thereto and allowed to react under an inert gas atmosphere, thereby generating an organic silicon compound having a repeating unit represented by general formula (2). On the other hand, p-t-butoxyhalobenzene or pyranylhalobenzene is reacted with an alkyllithium to prepare a lithium salt represented by general formula (3) in advance. Then, the organic silicon compound having a repeating unit represented by general formula (2) is allowed to react with the lithium salt represented by general formula (3), thereby synthesizing the organic silicon compound of the present invention having the repeating unit represented by general formula (I). In this reaction, the lithium salt represented by general formula (3) is used preferably in a ratio of one equivalent or more, and more preferably, in a ratio of 1.1 equivalent or more, relative to 1 equivalent of the organic silicon compound having the repeating unit represented by general formula (2).

wherein $R^2$ is the same as defined above.

wherein $R^1$, $R^3$ and k are the same as defined above.

Hereinbelow, examples of the organic silicon compounds of the present invention synthesized by the aforementioned method will be given.

wherein n represents degree of polymerization.

Since the organic silicon compound of the present invention can be quite easily decomposed by light, heat or acid, it is extremely suitable for a resist or a polymerization catalyst for the compound having an unsaturated bond.

Hereinbelow, the resist of the present invention will be described in detail.

The resist of the present invention has at least an organic silicon compound represented by general formula (I) and may further contain a compound which generates an acid upon exposure to light, if necessary. Because of good photoreactivity, the organic silicon compound can be used singly in resist. The resist containing an organic silicon compound represented by general formula (I) and a compound which generates an acid upon exposure to light is the so-called chemical-amplification type resist.

The organic silicon compound used in the resist of the present invention is preferred to have a degree of polymerization from about 5 to 50,000.

Examples of compounds which generate an acid upon exposure to light contained together with the organic silicon compound in the chemical-amplification type resist of the present invention include a sulfonium salt, an iodonium salt, a nitrobenzyl compound, naphthoquinonediazide-4-sulfonate and an azide compound. Among them, a sulfornium salt is particularly preferable. Examples of the compounds which generate an acid upon exposure to light (to be referred to as a photochemical acid generator) are more specifically shown below.

In the resist of chemical-amplification type mentioned above, the photochemical acid generator is contained preferably in the range of 0.01 to 30 wt %, and more preferably in the range of 0.5 to 5 wt % based on the amount of the organic silicon compound. This range is defined by the following reasons: If the content is below 0.01 wt %, the reaction between the acid generated upon exposure to light and the organic silicon compound will not be sufficiently carried out. In contrast, if the content exceeds 30 wt %, the storage stability of the resist will be prone to decrease.

The resist of the present invention as mentioned above can be prepared by dissolving the organic silicon compound, if necessary, together with the photochemical acid generator in an appropriate solvent. Specific examples of the organic solvents used herein include toluene, xylene, dimethylformamide, dimethylacetoamide and cellosolve.

To form a desired pattern using the resist of the present invention, the following method can be used. First, the resist of the present invention is coated on a substrate such as a silicon wafer by a spinner. The obtained coating is then prebaked at a temperature from about 70° to 120° C. and the solvent is allowed to evaporate to some extent, thereby obtaining a resist film. Subsequently, onto the surface of the resist film, light such as Deep UV light, KrF excimer laser light, electronic beam or x-ray is irradiated through a predetermined mask-pattern. After the completion of irradiation mentioned above, if desired, the resist may be hard-baked at a temperature of approximately 90° to 130° C. to accelerate the reaction of the organic silicon compound.

In the exposed part of the resist consisting of the organic silicon compound alone, the molecular weight of the organic silicon compound reduces since Si—Si bonds of the main chain thereof are decomposed due to the photoreactivity of the organic silicon compound itself. When the resist is subjected to the development using a solvent such as an alcohol as a developing solution and then washing, the exposed organic silicon compound whose molecular weight has been reduced is removed by dissolving in the developing solution, while the nonexposed portion is left unremoved, thereby forming a positive pattern. Since the organic silicon compound of the present invention exhibits a good photoreactivity, a high-precision pattern excellent in resolution can be formed even when it is used singly as the resist.

In the chemical-amplification type resist containing the organic silicon compound and the photochemical acid generator, Si—Si bonds of the main chain of the organic silicon compound are decomposed by the reaction with the acid generated in the exposed portion, and simultaneously, the t-butyl group or the pyranyl group of the side chain is removed to form the hydroxyl group. The organic silicon compound having the phenolic hydroxyl group can be soluble in an aqueous alkaline solution, so that development can be performed by using an aqueous alkaline solution. In this case, therefore, the resist of chemical-amplification type, successfully provides a high precision pattern improved in resolution compared to that formed of the organic silicon compound alone.

Hereinbelow, the thermal polymerization composition and photopolymerization composition of the present invention will be explained. These compositions contain a compound having an unsaturated bond and the organic silicon compound having a repeating unit represented by general formula (I).

The organic silicon compound used in the thermal polymerization composition and photopolymerization composition of the present invention is preferred to have a degree of polymerization of about 1 to 50,000 as mentioned above.

The compound having an unsaturated bond to be used in the thermal polymerization composition and photopolymerization composition of the present invention is not particularly limited as long as the compound can undergo radical polymerization by cleavage of unsaturated bonds. Usable compounds having an unsaturated bond are maleimide compounds represented by general formula (4) shown below, and acrylic compounds.

(4)

wherein, X is an alkylene group, cycloalkylene group, bivalent hydrocarbon group such as a monocyclic or a polycyclic arylene group, or a bivalent hydrocarbon group bonded through a bivalent atomic group such as —$CH_2$—, —CO—, —$SO_2$— or —CONH—.

Specific examples of the maleimide compounds include N,N'-phenylenebismaleimide, N,N'-hexamethylenebismaleimide, N,N'-methylene-di-p-phenylenebismaleimide, N,N'-oxy-di-p-phenylenebismaleimide, N,N'-4,4'-benzophenonebismaleimide, N'N-p-diphenylsulfonmaleimide, N,N'-(3,3'-dimethyl)methylene-di-p-phenylenebismaleimide, N,N'-(3,3'-diethyl)methylene-di-p-phenylenebismaleimide, and N,N'-methatoluylene-dimaleimide.

Examples of the acrylic compounds include acrylates such as 2-ethylhexyl acrylate, 1,6-hexanediol diacrylate, trimethylolpropane triacrylate and methacrylates corresponding to the above-mentioned acrylates.

In the thermal polymerization compound or photopolymerization compound of the present invention, the organic silicon compound is contained preferably in the range of 0.01 to 30 wt %, and more preferably in the range of 0.1 to 10 wt % based on the amount of the compound containing an unsaturated bond. This range is defined by the following reasons: If the content of the organic silicon compound is less than 0.01 wt %, polymerization of the compound having an unsaturated bond will not sufficiently proceed. In contrast, if the content exceeds 30 wt %, the influence of the remaining organic silicon compound used as a polymerization catalyst will be prone to be greater after the polymerization.

In the thermal polymerization composition or photopolymerization composition of the present invention, since radical species can be efficiently and easily generated by decomposing Si—Si bonds of the main chain of the organic silicon compound, the compound having an unsaturated bond can be polymerized with sufficient polymerization efficiency. The thermal polymerization composition of the present invention can be polymerized at a temperature of 200° C. or less, which is lower than the polymerization temperature of the thermal polymerization composition using a conventional polysilane as a polymerization catalyst. In addition, the thermal polymerization composition or photopolymerization composition of the present invention exhibits more excellent storage stability than that of a composition using an organic peroxide, imidazole compound, organic phosphorus compound as a polymerization catalyst. Furthermore, in the thermal polymerization composition or photopolymerization composition of the present invention, the polymerization temperature range of the compound having an unsaturated bond can be appropriately adjusted by controlling the skeleton and the bulkiness of an alkyl group, aryl group or aralkyl group to be introduced into a side chain of the organic silicon compound.

EXAMPLES

Hereinbelow, the present invention will be described in detail with reference to Examples.

Example 1

Synthesis of Organic Silicon Compound

First, phenylmethylpolysilane (10.4 g) having a degree of polymerization of 100 was dissolved in dry dichloromethane (150 ml). To this solution, trifluoromethanesulfonic acid (7.2 ml) was added at room temperature and the reaction was allowed to proceed for 3 hours under an argon atmosphere. After dichloromethane was removed under reduced pressure, tetrahydrofuran (80 ml) was added to the resultant solution. Subsequently, p-t-butoxyphenyllithium solution which is obtained by reacting p-t-butoxybromobenzene (20.1g) with a 1.6M hexane solution of n-butyllithium (104 ml), was added to this solution and the reaction was allowed to proceed for 1.5 hours at room temperature. The generated product was extracted by ethyl acetate (13 ml), followed by concentrating under reduced pressure and purified in methanol, thereby obtaining a white crystal (4.4 g).

Figure 1:
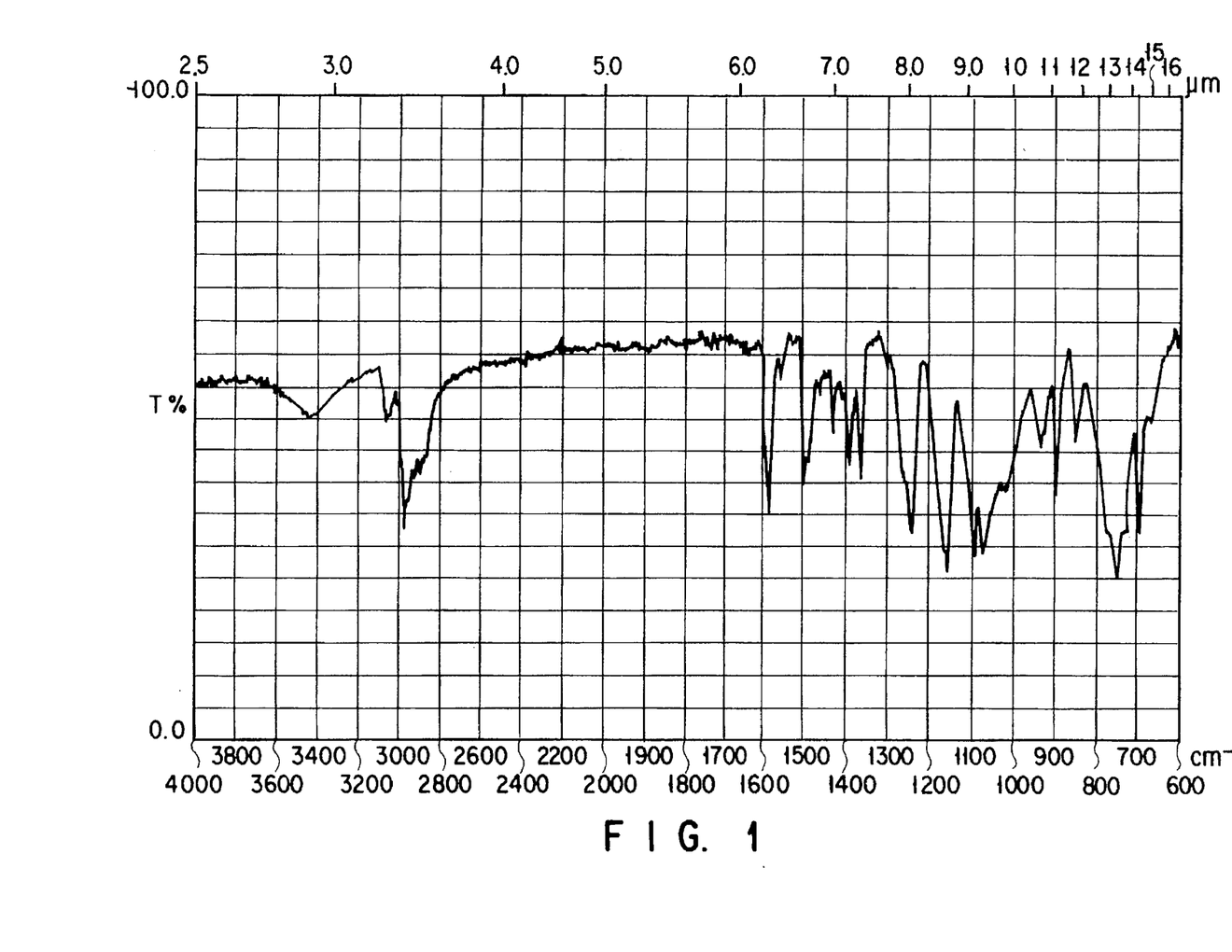
FIG. 1 is an IR spectrum of an organic silicon compound synthesized in Example 1.
Figure 2:
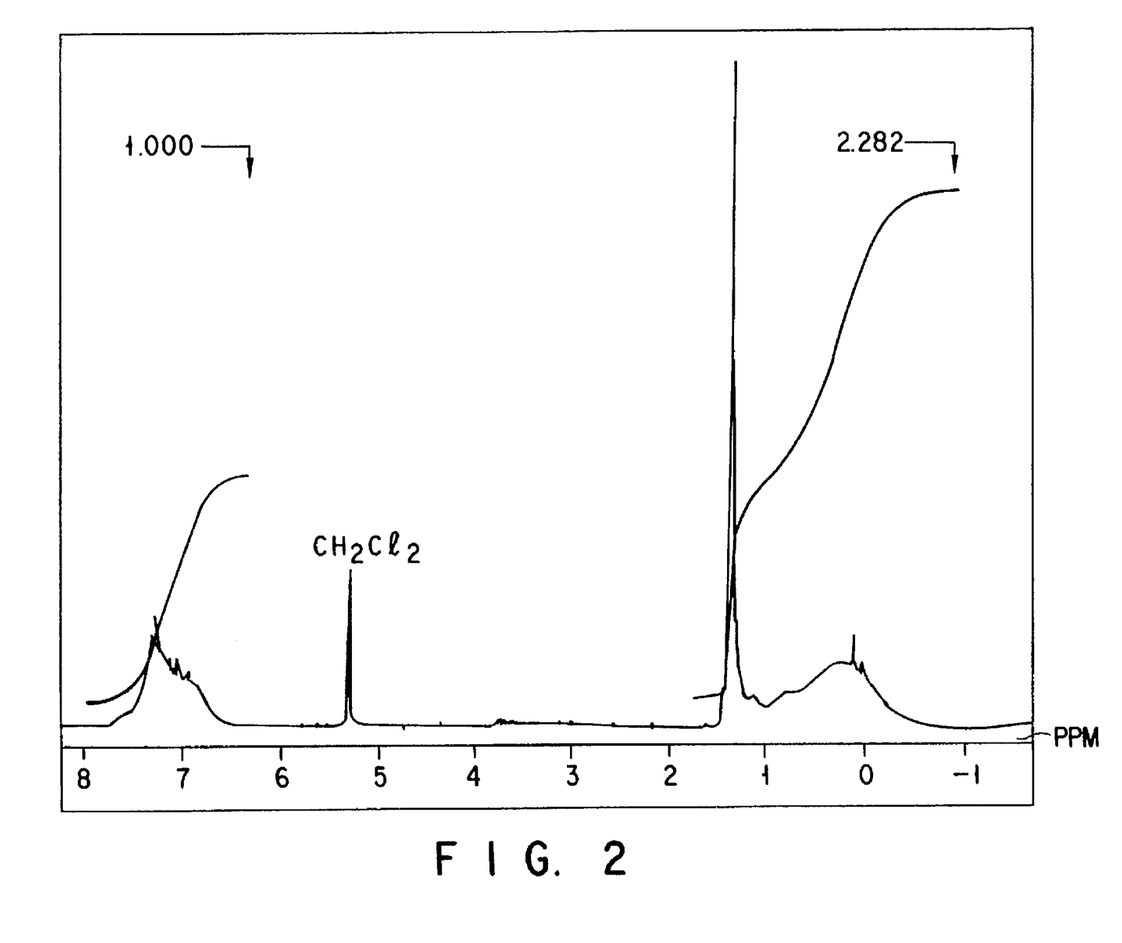
FIG. 2 is a $^1$H-NMR spectrum of an organic silicon compound synthesized in Example 1.
Figure 3:
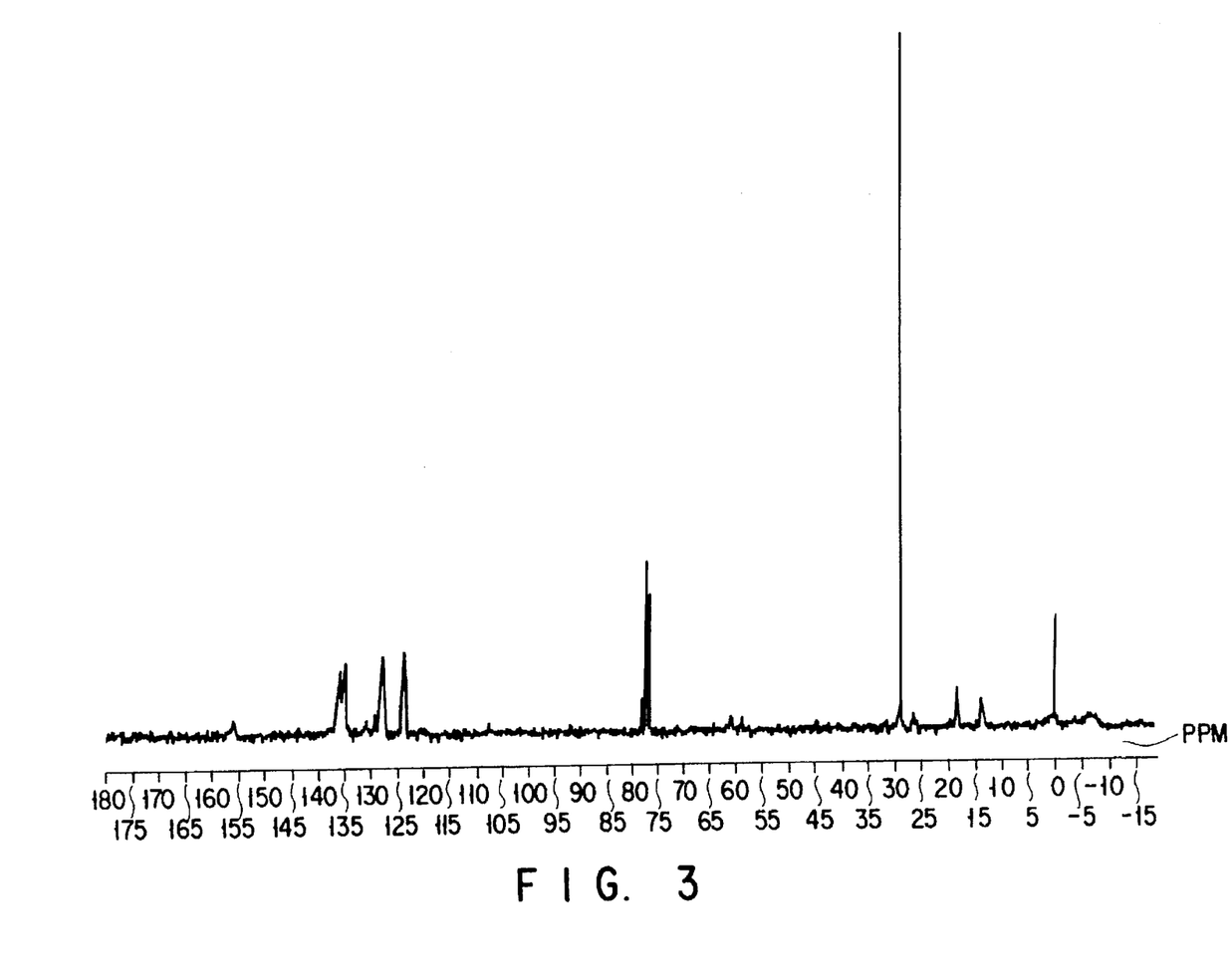
FIG. 3 is a $^{13}$C-NMR spectrum of an organic silicon compound synthesized in Example 1.
Figure 4:
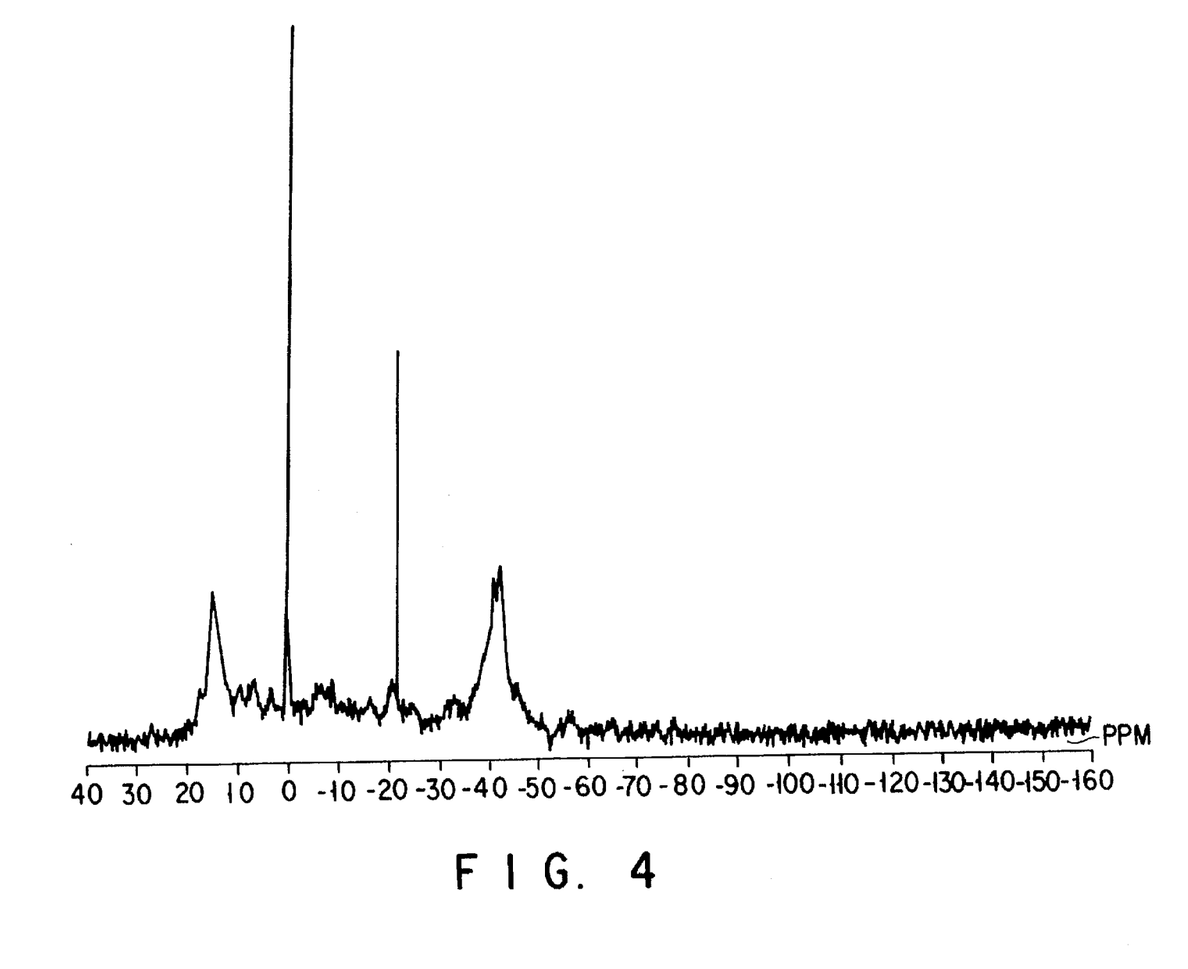
FIG. 4 is a $^{29}$Si-NMR spectrum of an organic silicon compound synthesized in Example 1.

IR spectrum, $^1$H-NMR spectrum, $^{13}$C-NMR spectrum and $^{29}$Si-NMR spectrum of the white crystal are shown in FIGS. 1 to 4. From these figures, it was confirmed that the obtained white crystal is polysilane having a repeating unit represented by the following chemical formula.

Average molecular weight: 7,000
Degree of polymerization: 60

Example 2

Application to Resist

Polysilanes represented by the following chemical formulas A to D were synthesized in the same manner as in Example 1. For comparison, conventional polysilanes represented by the following formulas E to G were also synthesized. On the other hand, compounds which generate an acid upon exposure to light (photochemical acid generator), represented by the following chemical formulas a to c, were prepared. Then, resists of sample Nos. 2-1 to 2-9 were prepared by dissolving polysilane and a photochemical acid generator in toluene in accordance with respective formulations indicated in Table 1 shown later.

Patterns were formed by subjecting the resists of Nos. 2-1 to 2-9 to coating onto a substrate, prebaking, exposure to patterned light, hard baking and development in successive order under the respective conditions shown in Table 1. The sensitivity, resolution and cross-sectional shape of the obtained patterns are also shown in Table 1. As is shown in Table 1, high-precision patterns excellent in resolution were successfully formed out of the resists of Nos. 2-1 to 2-6 which employed the polysilane of the present invention. Quite excellent patterns having a rectangular cross-sectional shape were obtained particularly in samples of Nos. 2-1 to 2-4 using the photochemical acid generator.

A:

Average molecular weight: 10,000
Degree of polymerization: 60

B:

Average molecular weight: 10,000
Degree of polymerization: 60

C:

Average molecular weight: 10,000
Degree of polymerization: 70

D:

Average molecular weight: 10,000
Degree of polymerization: 70

E:

Average molecular weight: 20,000
Degree of polymerization: 150

F:

Average molecular weight: 10,000
Degree of polymerization: 60

G:

Average molecular weight: 10,000
Degree of polymerization: 70 a:

having an unsaturated bond. In addition, polysilanes A and B used in Example 2 and conventional polysilane H represented by the following formula, were prepared as a polymerization catalyst.

As shown in Table 2, a bismaleimide compound (100 g) and a polysilane (1 g) were mixed to prepare thermal polymerization compositions of Nos. 3-1 to 3-5. The gelation time of each of thermal polymerization compositions was measured on hot plate at various temperatures. The results are shown in Table 2.

As is apparent from table 2, thermal polymerization compositions of Nos. 3-1 to 3-3 using the polysilane of the present invention can be sufficiently polymerized even in a temperature range of 200° C. or less. It is suggested that these polysilanes may have a latent property judging form the fact that the reaction abruptly proceeded at a certain temperature or more.

TABLE 1

|  |  | Example | | | | | | Comparative Example | | |
|---|---|---|---|---|---|---|---|---|---|---|
| Sample No. |  | 1 | 2 | 3 | 4 | 5 | 6 | 7 | 8 | 9 |
| Organic | A | 100 | — | — | — | 100 | — | — | — | — |
| silicon | B | — | 100 | — | — | — | 100 | — | — | — |
| compound | C | — | — | 100 | — | — | — | — | — | — |
| (part by | D | — | — | — | 100 | — | — | — | — | — |
| weight) | E | — | — | — | — | — | — | 100 | — | — |
|  | F | — | — | — | — | — | — | — | 100 | — |
|  | G | — | — | — | — | — | — | — | — | 100 |
| Photo- | a | 1 | 1 | — | — | — | — | 1 | — | — |
| chemical | b | — | — | 1 | — | — | — | — | — | — |
| acid | c | — | — | — | 1 | — | — | — | — | — |
| generator (part by weight) |  |  |  |  |  |  |  |  |  |  |
| Film thickness ($\mu$m) |  | 0.5 | 0.5 | 0.5 | 0.5 | 0.5 | 0.5 | 0.5 | 0.5 | 0.5 |
| Prebaking (temp./time) |  | 100° C./ 5 min. | 90°/ 5 min. | 90°C./ 5 min. | 110° C./ 5 min. | 100° C./ 5 min. | 90° C./ 5 min. | 90° C./ 5 min. | 90° C./ 5 min. | 90° C./ 5 min. |
| Light source |  | EB | KrF | KrF | EB | EB | KrF | KrF | EB | KrF |
| (Sensitivity: amount of exposure #1) |  | (5) | (70) | (30) | (5) | (5) | (70) | (60) | (5) | (30) |
| Sample |  | 1 | 2 | 3 | 4 | 5 | 6 | 7 | 8 |  |
| Hard baking (temp./time) |  | 110° C./ 1 min. | 110° C./ 1 min. | 110° C./ 1 min. | 130° C./ 1 min. | 110° C./ 1 min. | 110° C./ 1 min. | 110° C./ 1 min. | 110° C./ 1 min. | 110° C./ 1 min. |
| Developing solution #2 |  | β | β | β | β | α | α | α | α | α |
| Developing time (sec.) |  | 90 | 100 | 60 | 80 | 90 | 90 | 90 | 100 | 100 |
| Resolution ($\mu$m) |  | 0.3 | 0.3 | 0.3 | 0.3 | 0.5 | 0.5 | 0.6 | 0.7 | 0.7 |
| Pattern cross-sectional shape |  | rectangle | rectangle | rectangle | rectangle | trapezoid | trapezoid | triangle | triangle | triangle |

1: unit: in the case of KrF mJ/cm² (sample Nos. 2, 3, 6, 7, 9)
in the case of EB μC/cm² (sample Nos. 1, 4, 5, 8)
2: Developing solution α . . . i-propanol/cyclohexane mixed solution (weight ratio: 1:1)
β . . . TMAH (tetramethylammonium hydroxide) aqueous solution (2.38 wt. %)

Example 3

Application to Thermal Polymerization Composition

Bismaleimide compounds X, Y and Z represented by the following chemical formulas were prepared as a compound

TABLE 2

| Sample No. | | Example | | | Comparative Example | |
|---|---|---|---|---|---|---|
| | | 3-1 | 3-2 | 3-3 | 3-4 | 3-5 |
| bismaleimide | X | 100 | — | — | 100 | — |
| (parts by weight) | Y | — | 100 | — | — | 100 |
| | Z | — | — | 100 | — | — |
| polysilane | A | 1 | — | 1 | — | — |
| (part by weight) | B | — | 1 | — | — | — |
| | H | — | — | — | 1 | 1 |
| gelation time at | 170° C. | >20 min | >20 min | >20 min | >20 min | >20 min |
| | 180° C. | 64 sec | 60 sec | 65 sec | 20 min | 20 min |
| | 200° C. | 43 sec | 40 sec | 45 sec | 150 sec | 160 sec |
| | 220° C. | 20 sec | 15 sec | 20 sec | 100 sec | 120 sec |

Further, thermal polymerization composition of No. 3-1 was dissolved in 1,4-dioxane (400 g) and allowed to stand still for several days at room temperature. The composition exhibited a good storage stability without particular changes.

On the other hand, the similar storage stability test was applied to the thermal polymerization composition prepared in the same manner as in the preparation of sample No. 3-1 except that an organic peroxide represented by the following formula was used instead of polysilane A of the present invention. In the thermal polymerization composition allowed to stand still for 24 hours, the polymerization proceeded and a precipitate insoluble in 1,4-dioxane was generated.

From the results in the foregoing, it was confirmed that the thermal polymerization composition using the polysilane of the present invention as a polymerization catalyst exhibited an excellent storage stability compared to that using a peroxide.

Example 4

Application to Photopolymerization Composition

Methacrylates P, Q and R represented by the following chemical formulas were prepared as a compound having an unsaturated bond. In addition, the polysilanes of the present invention, B and C used in Example 2 and conventional polysilane H were prepared as a polymerization catalyst.

A methacrylate and a polysilane were mixed in accordance with the formulations shown in Table 3 to prepare photopolymerization compositions of Nos. 4-1 to 4-4.

Subsequently, each of the photopolymerization compositions was coated onto an aluminum substrate. Onto the coating, ultraviolet light was irradiated from a high-pressure mercury lamp positioned at 15 cm apart, in an irradiation amount of 80 w/cm for 10 seconds to polymerize the methacrylate.

As a result, tack-free coatings were obtained from samples of Nos. 4-1 to 4-3 which employed the polysilane of the present invention as a polymerization catalyst. Whereas, the coating formed of sample No. 4-4 using a conventional polysilane was slightly tacky.

From the results in the foregoing, it was found that the photopolymerization composition exhibiting sufficient polymerization efficiency can be obtained by using the polysilane of the present invention as a polymerization catalyst for a compound having an unsaturated bond.

TABLE 3

| Sample No. | | Example | | | Comparative Example |
|---|---|---|---|---|---|
| | | 4-1 | 4-2 | 4-3 | 4-4 |
| methacrylate (parts by weight) | P | 20 | — | — | 20 |
| | Q | — | 20 | — | — |
| | R | — | — | 40 | — |
| polysilane (parts by weight) | B | 1 | — | 1 | — |
| | C | — | 1 | — | — |
| | H | — | — | — | 1 |

What is claimed is:

1. An organic silicon compound having a repeating unit represented by general formula (I) shown below:

(I)

wherein $R^1$ is a tetrahydropyranyl group, $R^2$ is an hydrogen atom, an alkyl group having 1 to 24 carbon atoms, an aryl group having 6 to 24 carbon atoms, or an aralkyl group having 7 to 24 carbon atoms, $R^3$ is an alkyl group having 1 to 24 carbon atoms, an aryl group having 6 to 24 carbon atoms, an aralkyl group having 7 to 24 carbon atoms or an alkoxyl group, and k represents an integer from 0 to 4.

2. A resist comprising
an organic silicon compound having a repeating unit represented by general formula (I) shown below:

(I)

wherein $R^1$ is a tetrahydropyranyl group, $R^2$ is an hydrogen atom, an alkyl group having 1 to 24 carbon atoms, an aryl group having 6 to 24 carbon atoms, or an aralkyl group having 7 to 24 carbon atoms, $R^3$ is an alkyl group having 1 to 24 carbon atoms, an aryl group having 6 to 24 carbon atoms, an aralkyl group having 7 to 24 carbon atoms or an alkoxyl group, and k represents an integer from 0 to 4.

3. The resist according to claim 2, wherein said organic silicon compound has a degree of polymerization of 5 to 50,000.

4. The resist according to claim 3, wherein said organic silicon compound has a degree of polymerization of 20 to 10,000.

5. The resist according to claim 2, further comprising a compound which generates an acid upon exposure to light.

6. The resist according to claim 5, wherein said compound which generates an acid upon exposure to light is contained in the range of 0.01 to 30 wt % based on the amount of the organic silicon compound.

7. The resist according to claim 6, wherein said compound which generates an acid upon exposure to light is contained in the range of 0.5 to 5 wt % based on the amount of the organic silicon compound.

8. A thermal polymerization or photopolymerization composition comprising, in admixture,
a compound having an unsaturated bond,
an organic silicon compound having a repeating unit represented by general formula (I) shown below:

(I)

wherein $R^1$ is a t-butyl group or a tetrahydropyranyl group, $R^2$ is an hydrogen atom, an alkyl group having 1 to 24 carbon atoms, an aryl group having 6 to 24 carbon atoms, or an aralkyl group having 7 to 24 carbon atoms, $R^3$ is an alkyl group having 1 to 24 carbon atoms, an aryl group having 6 to 24 carbon atoms, an aralkyl group having 7 to 24 carbon atoms or an alkoxyl group, and k represents an integer from 0 to 4.

9. The composition according to claim 8, wherein said compound having an unsaturated bond is a maleimide compound or an acrylic compound.

10. The composition according to claim 8, wherein said organic silicon compound is contained in the range of 0.01 to 30 wt % based on the amount of the compound having an unsaturated bond.

11. The composition according to claim 10, wherein said organic silicon compound is contained in the range of 0.1 to 10 wt % based on the amount of the compound having an unsaturated bond.

12. The composition according to claim 8, wherein said organic silicon compound has a degree of polymerization of 1 to 50,000.

13. The composition according to claim 12, wherein said organic silicon compound has a degree of polymerization of 5 to 10,000.

* * * * *